(12) United States Patent
Hasbun

(10) Patent No.: US 11,617,502 B2
(45) Date of Patent: Apr. 4, 2023

(54) ADJUSTABLE LARYNGOSCOPE SYSTEM AND METHOD OF USE

(71) Applicant: William Miguel Hasbun, Mount Laurel, NJ (US)

(72) Inventor: William Miguel Hasbun, Mount Laurel, NJ (US)

(*) Notice: Subject to any disclaimer, the term of this patent is extended or adjusted under 35 U.S.C. 154(b) by 0 days.

(21) Appl. No.: 17/817,107

(22) Filed: Aug. 3, 2022

(65) Prior Publication Data

US 2022/0369917 A1 Nov. 24, 2022

Related U.S. Application Data

(63) Continuation-in-part of application No. 17/010,996, filed on Sep. 3, 2020.

(60) Provisional application No. 62/973,016, filed on Sep. 11, 2019.

(51) Int. Cl.
| | |
|---|---|
| *A61B 1/267* | (2006.01) |
| *A61B 1/00* | (2006.01) |
| *A61B 1/07* | (2006.01) |
| *A61B 1/06* | (2006.01) |

(52) U.S. Cl.
CPC .......... *A61B 1/267* (2013.01); *A61B 1/00101* (2013.01); *A61B 1/00105* (2013.01); *A61B 1/0669* (2013.01); *A61B 1/07* (2013.01)

(58) Field of Classification Search
CPC .................................................. A61B 1/267
See application file for complete search history.

(56) References Cited

U.S. PATENT DOCUMENTS

| | | | |
|---|---|---|---|
| 2,289,226 A * | 7/1942 | Von Foregger | A61B 1/267 600/199 |
| 4,384,570 A | 5/1983 | Roberts | |
| 4,947,829 A | 8/1990 | Bullard | |
| 4,958,624 A | 9/1990 | Stone et al. | |
| 5,070,859 A * | 12/1991 | Waldvogel | A61B 1/267 600/185 |
| 5,893,830 A | 4/1999 | Zeitels | |
| 2003/0018239 A1* | 1/2003 | Cartledge | A61B 1/267 600/199 |
| 2003/0120131 A1* | 6/2003 | Pecherer | A61B 1/267 600/199 |
| 2008/0300464 A1* | 12/2008 | Dhingra | A61B 1/267 600/199 |
| 2009/0264708 A1 | 10/2009 | Pacey et al. | |

FOREIGN PATENT DOCUMENTS

CN 102273999 7/2013

* cited by examiner

*Primary Examiner* — Christian A Sevilla
(74) *Attorney, Agent, or Firm* — LaMorte & Associates, P.C.

(57) ABSTRACT

A laryngoscope system that consists of a blade assembly and a handle assembly. The blade assembly has a blade body with multiple handle attachment points. The handle can attach to any of the handle attachment points using a standard ISO 7376 connection. By attaching the handle to different handle attachment points the functional length of the laryngoscope blade can be adjusted. The handle that attaches to the blade body can contain an internal lighting unit. If so, the blade body contains optical elements at the handle attachment points that direct light from the handle to a forward facing output. If the handle does not hold a light, a lighting unit can be added to the blade body.

17 Claims, 7 Drawing Sheets

ADJUSTABLE LARYNGOSCOPE SYSTEM AND METHOD OF USE

RELATED APPLICATIONS

This application is a continuation-in-part of U.S. patent application Ser. No. 17/010,996 filed Sep. 3, 2020, which claims the benefit of Provisional Patent Application No. 62/973,016 filed Sep. 11, 2019.

BACKGROUND OF THE INVENTION

1. Field of the Invention

In general, the present invention relates to the structure of laryngoscopes. More particularly, the present invention relates to the improved structure of blades and handles that form a laryngoscope.

2. Prior Art Description

It is not uncommon for an emergency medical technician, field medic or other first responder to encounter a patient that is unconscious or otherwise unresponsive. If the patient is not breathing, it is often necessary to maintain a patient's airway. This can be achieved by inserting an endotracheal tube through the patient's mouth and into the patient's trachea. A properly placed endotracheal tube establishes an open pathway for air to pass into the patient's lungs that cannot be obstructed by bleeding or swelling. The most common difficulty in inserting an endotracheal tube is positioning the endotracheal tube in the patient's trachea, which leads to the lungs, rather than in the patient's esophagus which leads to the stomach. In order to properly position the endotracheal tube, a laryngoscope is commonly used. The laryngoscope enables a medical professional to see into the throat and visually verify the placement of the endotracheal tube. The observation of a patient's throat using a laryngoscope is referred to as laryngoscopy.

A modern laryngoscope includes a handle and a blade. Often the blade is detachable from the handle. In use, the blade is inserted inside the patient's mouth and partially down the patient's throat to create a direct line of sight into the throat. The blade applies pressure to soft tissue of the throat as well as aligns the patient's head and neck in order to create a direct line of sight. Laryngoscopes can have a variety of blades. Early laryngoscopes used straight blades that are often called Magill blades. This blade shape is difficult to control in adult humans and can cause pressure on the vagus nerve. However, this design is still used in veterinary applications.

Most modern laryngoscope blades that are used on humans are curved blades. The Macintosh blade is the most widely used of the curved laryngoscope blades. However, a variety of other curved blade styles exist. Both straight blades and curved blades are available in assorted sizes for different applications. For human use, the sizes typically vary from size "0" for neonatal use to size "4" for large adults. An incorrectly sized laryngoscope can cause harm to a patient, including trauma to the front incisors caused by blade contacting the teeth.

A problem therefore exists for first responders who must carry medical equipment to the location of a patient. First responders may bring a laryngoscope and an endotracheal tube. However, the laryngoscope is often a number "2" or "3" laryngoscope blade so as to be usable on an average sized person. Such a laryngoscope may not be appropriate for children, small woman, or large men. The only solution is for the first responder to carry multiple laryngoscope blades, which may be impractical for many first responders, such as military medics.

In the prior art, there have been laryngoscopes that have blades that can be adjusted in length. Such blades are exemplified by CN 2584126. The problem with such blades is that they require a specialty handle that enables the blade to adjust. This prevents the commercialization of the device because the connections between a laryngoscope and a laryngoscope handle have become internationally standardized in ISO 7376. The standard connections needed on all blades and all blade handles prevent prior art adjustment schemes from being effectively implemented.

A need therefore exists for an improved laryngoscope with a blade that can be selectively adjusted in size and wherein both the blade and handle conform to the international standards set forth in ISO 7376. This need is met by the present invention as described and claimed below.

SUMMARY OF THE INVENTION

The present invention is a laryngoscope system that consists of a blade assembly and a handle assembly. The blade assembly has a blade body with multiple handle attachment points. The handle can attach to any of the handle attachment points using a standard ISO 7376 connection. By attaching the handle to different handle attachment points the functional length of the laryngoscope blade can be adjusted. Preferably, the adjustments enable the blade to be adjusted to match the functional length of a standard number one laryngoscope blade, a number two laryngoscope blade, a number three laryngoscope blade and a number four laryngoscope blade.

The handle that attaches to the blade body can contain an internal lighting unit. If so, the blade body contains optical elements at the handle attachment points that direct light from the handle to a forward facing output. If the handle does not hold a light, a lighting unit can be added to the blade body.

BRIEF DESCRIPTION OF THE DRAWINGS

For a better understanding of the present invention, reference is made to the following descriptions of exemplary embodiments thereof, considered in conjunction with the accompanying drawings, in which.

DETAILED DESCRIPTION OF THE DRAWINGS

Although the present invention system can be embodied in many ways, only a few exemplary embodiments are illustrated. The exemplary embodiments are being shown for the purposes of explanation and description. The exemplary embodiments are selected in order to set forth some of the best modes contemplated for the invention. The illustrated embodiments, however, are merely exemplary and should not be considered limitations when interpreting the scope of the claims.

Figure 1:
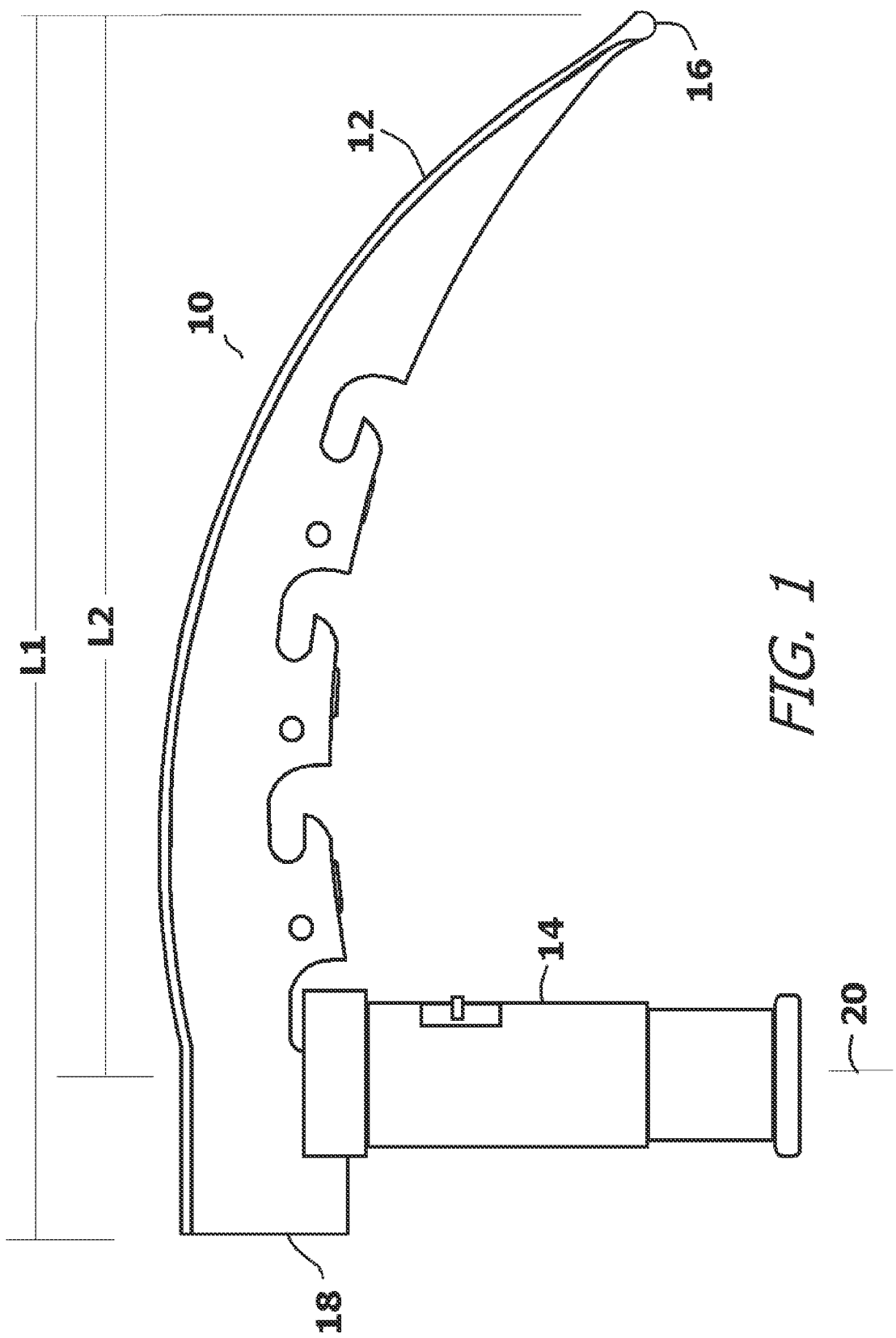
FIG. 1 shows an exemplary embodiment of a laryngoscope system with adjustable blade and handle assemblies.
Figure 2:
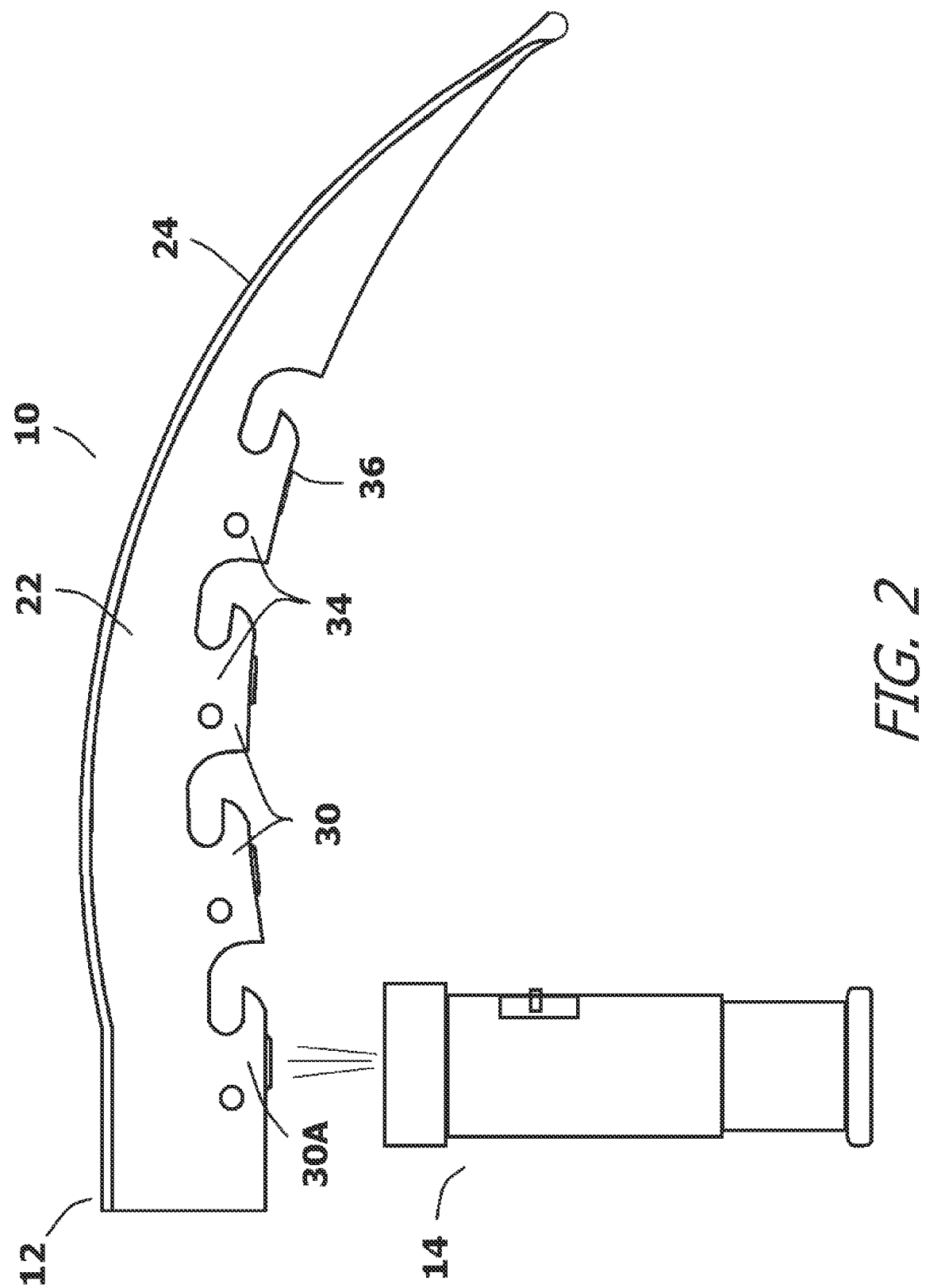
FIG. 2 shows the exemplary embodiment of FIG. 1 with the handle assembly separated from the blade assembly.

Referring to FIG. 1 in conjunction with FIG. 2, a laryngoscope system 10 is shown. The laryngoscope system 10 has a blade assembly 12 and a handle assembly 14 that selectively interconnect. The connection between the blade assembly 12 and the handle assembly 14 conforms to the ISO 7376 standard for such connections. Accordingly, the blade assembly 12 can be used with any standardized laryngoscope handle and the handle assembly 14 can be used with any standardized laryngoscope blade. As will be later explained in more detail, the blade assembly 12 has a distal end 16 that extends into the throat, an opposite second end 18, and a length L1 that extends between the distal end 16 and the second end 18. The handle assembly 14 is formed around a mid-axis 20. When the handle assembly 14 is attached to the blade assembly 12, there is a second length L2 between the mid-axis 20 of the handle assembly 14 and the distal end 16 of the blade assembly 12. This second length L2 can be selectively adjusted so that the second length L2 can be equal in length to a standard number one, number two, number three, or number four laryngoscope blade. In this manner, only the one blade assembly 12 need be carried, and that blade assembly 12 can be properly adjusted in size to the patient in need.

Figure 3:
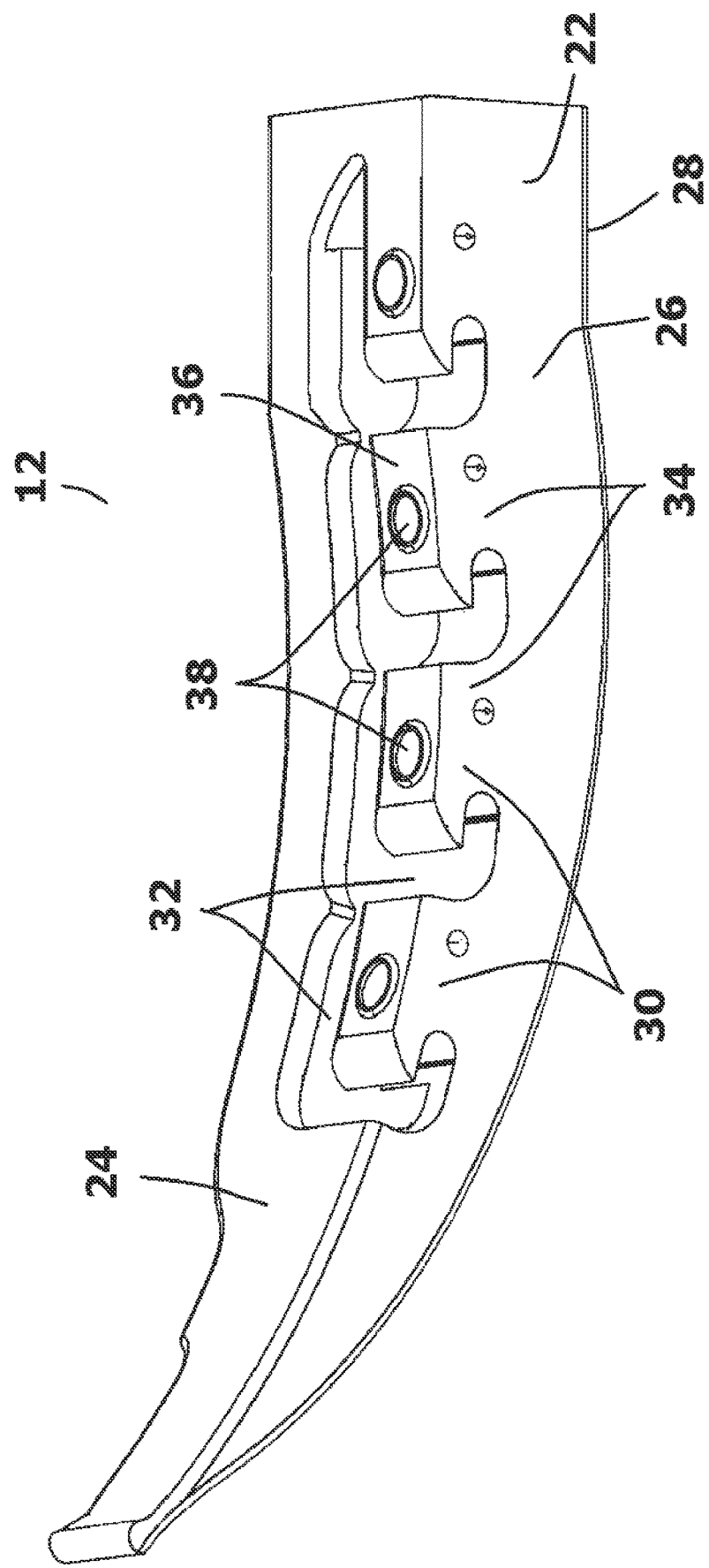
FIG. 3 shows a perspective view of the blade assembly used in the exemplary embodiment of FIG. 1.
Figure 4:
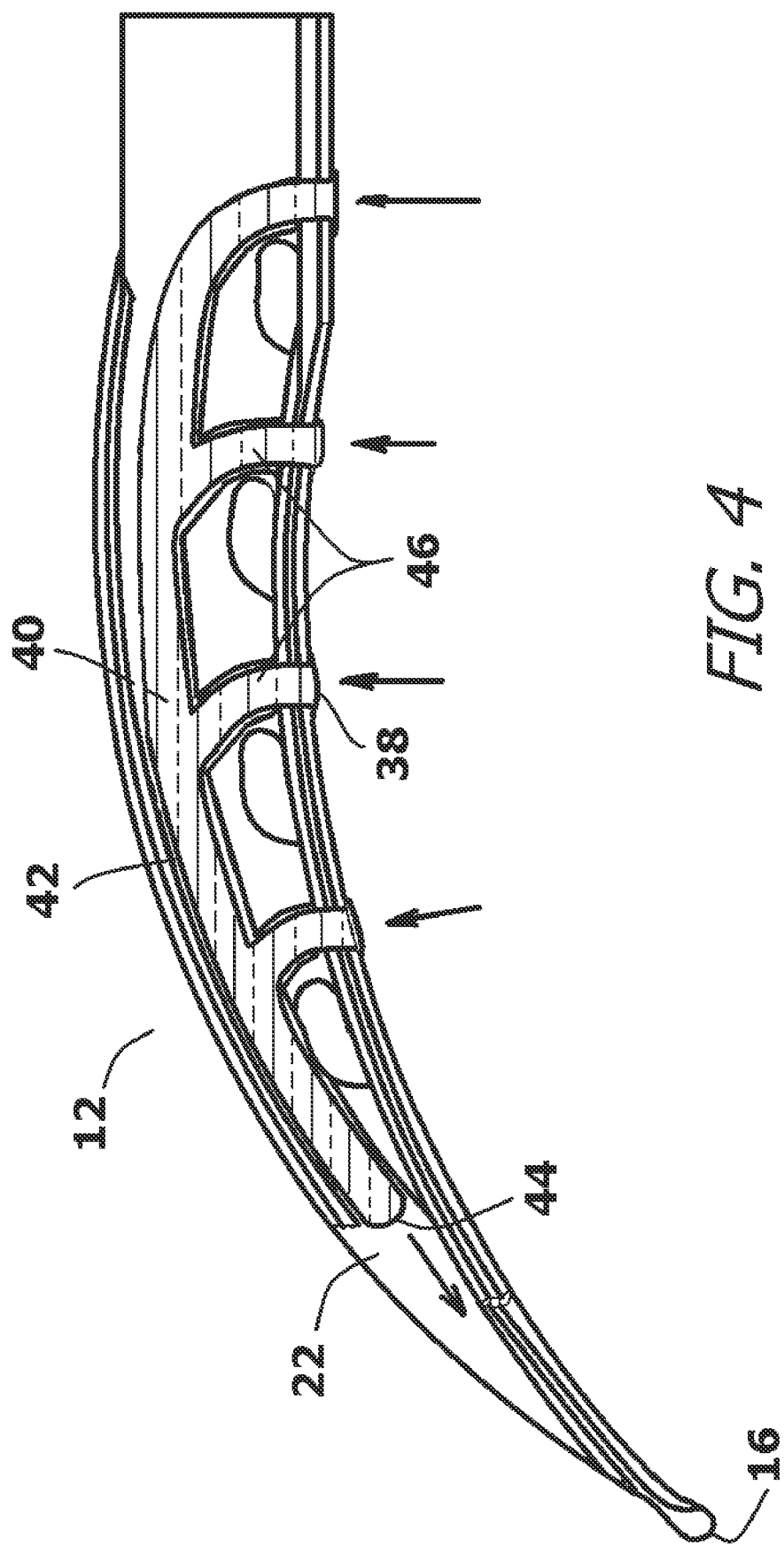
FIG. 4 is a cross-sectional view of the blade assembly viewed along section line 4-4 in FIG. 3.

Referring to FIG. 3 and FIG. 4 in conjunction with FIG. 1 and FIG. 2, it can be seen that the blade assembly 12 includes a blade body 22. In the shown embodiment the blade body 22 is a curved. However, it will be understood that in alternate embodiments, the blade body 22 can be straight. The blade body 22 has a spatula surface 24 that is supported by a side wall 26 and a top flange 28. During use, the inner spatula surface 24 presses against the tongue. A plurality of handle connections 30 are formed into the blade body 22. Each of the handle connections 30 is a standardized handle connection as defined in ISO 7376. Accordingly, each of the handle connections 30 is capable of interconnecting with a standardized laryngoscope handle being commercially sold. The handle connections 30 are spaced. In the shown embodiment, there are four handle connections 30. When the handle assembly 14 is attached to the first of the handle connections 30A, the distance between the handle assembly 14 and the distal end 16 of the blade body 22 is equal to that of a number one sized blade. Likewise, the second, third and fourth handle connections 30 result in lengths equal to number two, number three, and number four blade lengths, respectively.

The formation of the handle connections 30 in the blade body 22 produces slots 32 in the spatula surface 24 and the side wall 26 of the blade body 22. The slots 32 define mounting peninsulas 34 on the blade body 22. Each of the mounting peninsulas 34 has a bottom surface 36 that follows the same curvature as the overall spatula surface 24. The bottom surface 36 of a mounting peninsula 34 is covered by the handle assembly 14 when the handle assembly 14 is attached to that mounting peninsula 34. A port opening 38 is formed in the bottom surface 36 of each of the mounting peninsulas 34.

As is primarily shown in FIG. 4, a fiber optic bundle 40 is mounted to the blade body 22 to complete the blade assembly 12. A groove 42 is molded into the blade body 22 to receive and retain the fiber optic bundle 40. The fiber optic bundle 40 has a single output end 44 that points in the same direction as the distal end 16 of the blade body 22. The fiber optic bundle 40 also has branches 46, wherein each branch 46 leads to a different port opening 38. In this manner, if light is shown into any of the port openings 38, the fiber optic bundle 40 directs the light to the output end 44. In this manner, if a handle assembly 14 with an internal light is attached to any of the handle connections 30, light can be transferred from the handle assembly 14 to the distal end 16 of the blade assembly 12.

Figure 5:
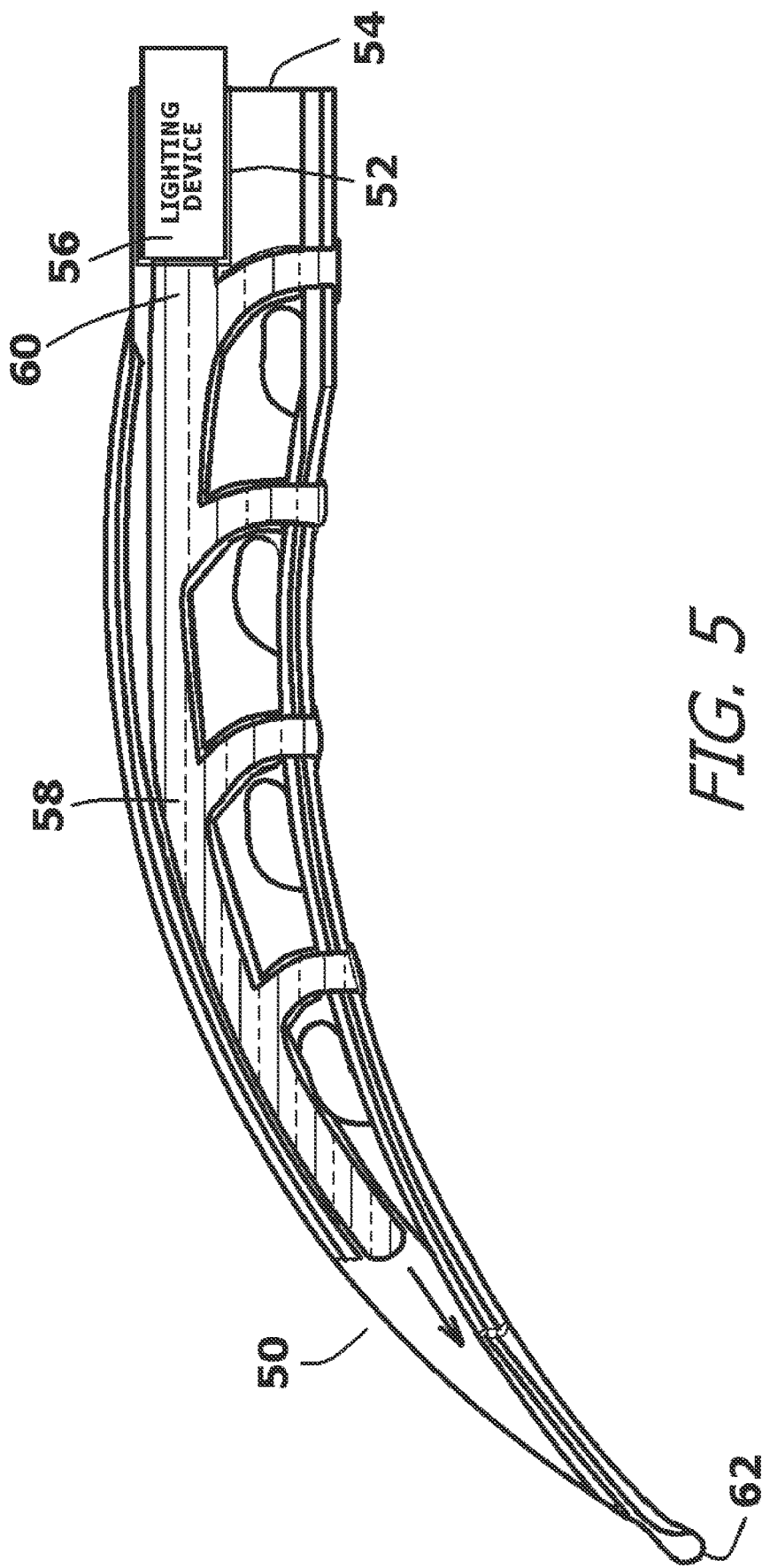
FIG. 5 is a cross-sectional view of an alternate embodiment of a blade assembly that can be used as part of the laryngoscope system.

Not all standardized laryngoscope handles contain internal lights. If a laryngoscope handle without a light is going to be used, the blade assembly must contain its own light source. Referring to FIG. 5, an alternate embodiment of a blade assembly 50 is shown. The blade assembly 50 has a receptacle 52 at a second end 54 for receiving a small lighting device 56. A fiber optic bundle 58 is provided that has an extra branch 60 that extends to the receptacle 52. In this manner, light from the lighting device 56 can propagate through the fiber optic bundle 58 and be directed toward the distal end 62 of the blade body 22.

Figure 7:
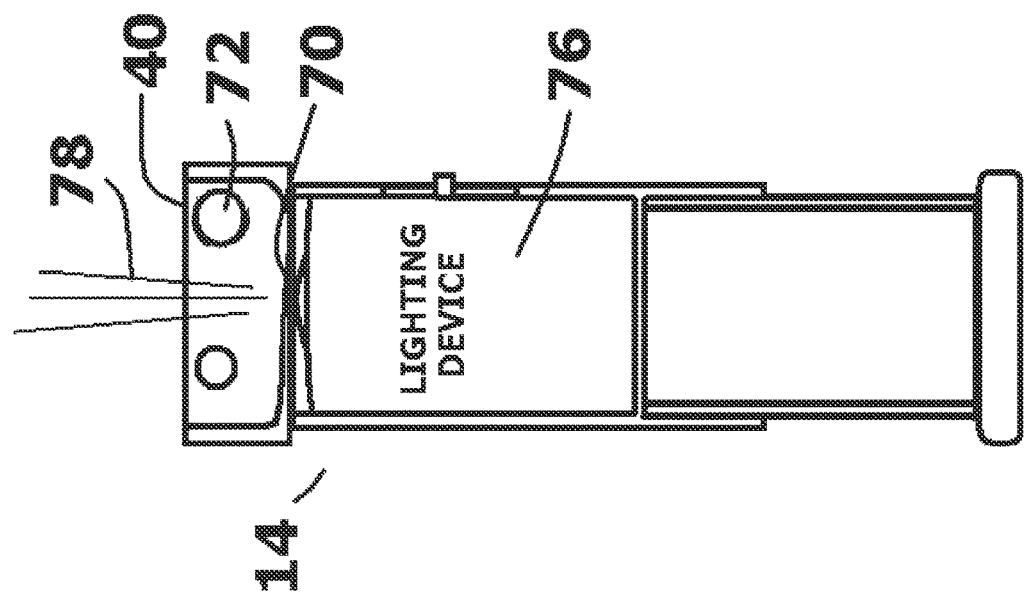
FIG. 7 is a cross-sectional view of the handle assembly.
Figure 6:
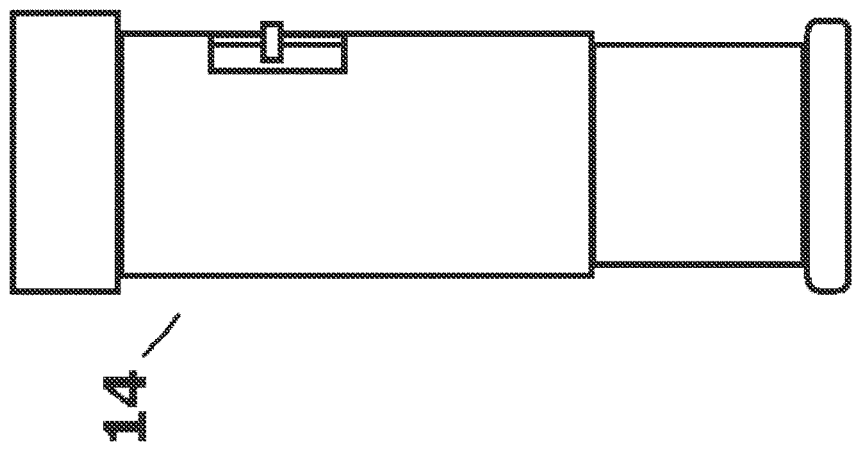
FIG. 6 is an exploded view of the handle assembly used in the exemplary embodiment of FIG. 1.

Referring to FIG. 6 and FIG. 7 in conjunction with FIG. 1 and FIG. 2, the details of the handle assembly 14 are described. The handle assembly 14 has a top end 70 with a connector 72 that conforms to the ISO 7376 connector standard. The connector 72 is capable of mechanically interconnecting with any of the handle connections 30 on the blade assembly 12 that have been previously described. A light port 74 is formed in the the handle assembly 14. The light port 74 enables light produced within the handle assembly 14 to shine out of the handle assembly 14. When the handle assembly 14 is attached to the blade assembly 12, such as in FIG. 1, the light port 74 on the handle assembly 14 aligns with one of the port openings 38 on the blade assembly 12.

The handle assembly 14 retains a lighting device 76. The lighting device 76 can be an auxiliary flashlight or a light and battery assembly that is integrated into the structure of the handle assembly 14. In either scenario, the lighting device 76 creates a strong beam of light 78 that is directed out of the light port 74. The handle assembly 14 must be long enough to comfortably grip with one hand. Thus, the lighting device 76 can be made shorter than the handle assembly 14. This leaves room for a storage compartment 80. The storage compartment 80 can contain accessories that can be used in conjunction with the handle assembly 14 other than the blade assembly 12. Such accessories can include otoscope attachments, tongue depressor attachments, and the like.

Figure 8:
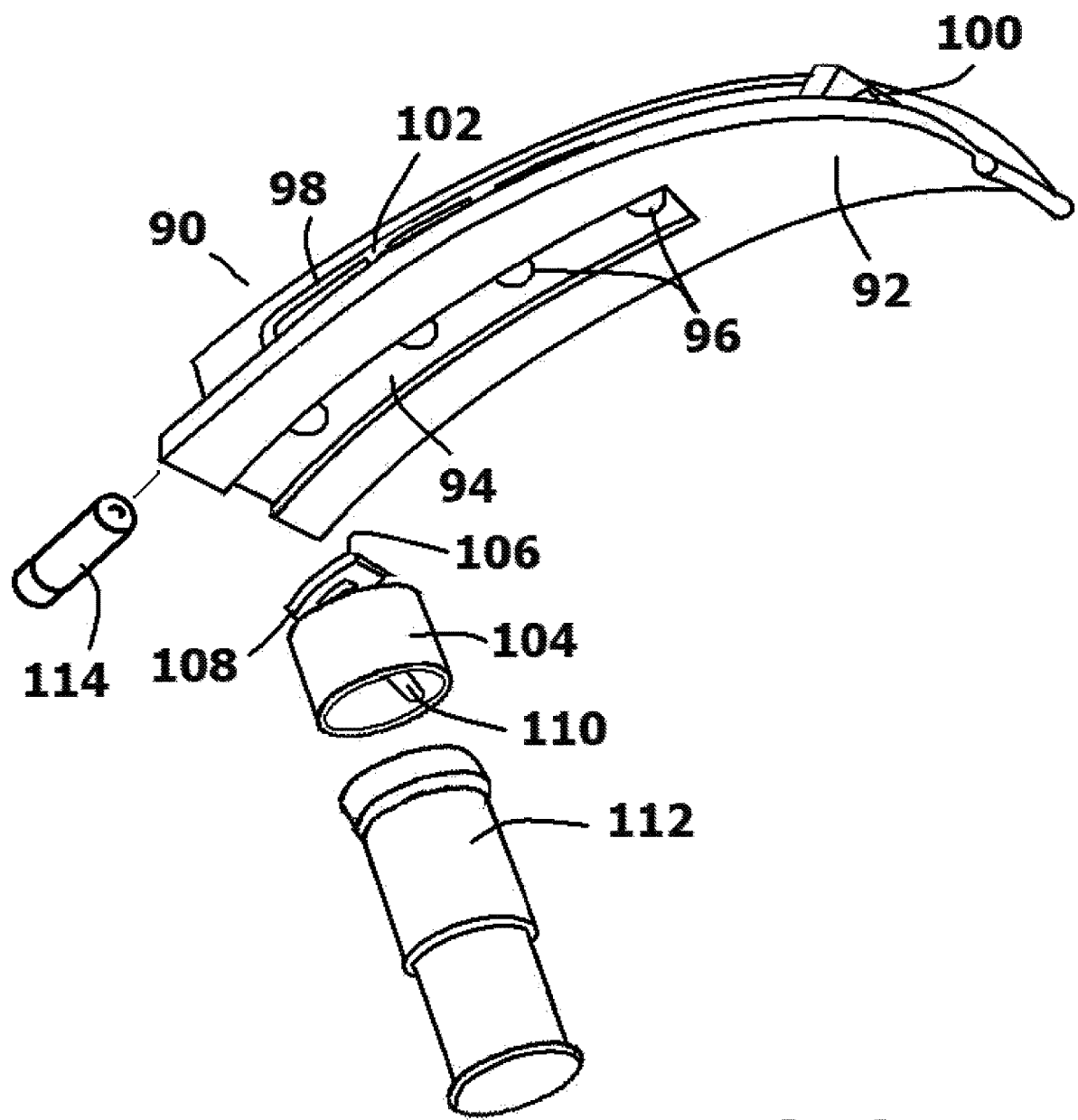
FIG. 8 shows an alternate embodiment of a laryngoscope system.

In the previous embodiments, the blade assembly 12 and the handle assembly 14 are constructed to the current ISO 7376 standards for attachment. This need not be the case. Smaller, lighter blade assemblies can be made that do not themselves adhere to the ISO connection standards. Rather, an adapter can be used to interconnect the blade assembly to a standard handle. Such an alternate system is described below. Referring to FIG. 8, an alternate blade assembly 90 is shown that has a spatula surface 92. A T-slot 94 is formed in the spatula surface 92. A plurality of port openings 96 are disposed within the T-slot 94. A fiber optic bundle 98 is provided that has an output end 100. Branches 102 extend from the fiber optic bundle 98 that lead to each of the port openings 96.

An adapter 104 is provided. The adaptor 104 has a first end 106 with a T-shaped connector 108 that engages the T-slot 94 in the blade assembly 90. The opposite second end of the adaptor contains a standard ISO 7376 connector 110 that can attach to any standard laryngoscope handle in the conventional manner.

It will be understood that the embodiments of the present invention that are illustrated and described are merely exemplary and that a person skilled in the art can make many variations to those embodiments. For instance, the style of the blade can be changed to any known straight or curved shape. All such embodiments are intended to be included within the scope of the present invention as defined by the claims.

What is claimed is:

1. A laryngoscope system, comprising:
   a blade body having a distal end and an opposite second end;
   a handle;
   wherein said handle can be selectively attached to said blade body at a plurality of attachment points between said distal end and said second end.

2. The system according to claim 1, further including port openings formed in said blade body at each of said plurality of attachment points.

3. The system according to claim 2, further including an optical fiber bundle supported by said blade body that direct light entering said port openings to an output, wherein said output is oriented toward said distal end of said blade body.

4. The system according to claim 3, wherein said blade body has a receptacle for receiving a lighting device at said second end, wherein said optical fiber bundle further direct light from said receptacle to said output.

5. He system according to claim 3, further including a lighting device supported by said body blade, wherein said optical fiber bundle further direct light from said lighting device to said output.

6. The system according to claim 3, wherein said handle contains a lighting device that shines light into said an optical fiber bundle through one of said port openings when said handle is attached to said blade body.

7. The system according to claim 1, further including an adaptor that selectively attaches to said blade body at one of said attachment points, wherein said handle attaches to said adapter.

8. The system according to claim 1, wherein said attachment points are at different distances from said distal end of said blade body, wherein said different distances correspond in length to standard sizes of laryngoscope blades.

9. A blade assembly for a laryngoscope, comprising:
   a blade body having a distal end, an opposite second end, and a spatula surface extending between said distal end and said second end, wherein a plurality of handle attachment points are disposed along said spatula surface;
   an optical fiber bundle connected to said blade body that channels light directed at said plurality of handle attachment points to a common output.

10. The blade assembly according to claim 9, wherein said common output is directed toward said distal end of said blade body.

11. The blade assembly according to claim 9, wherein said blade body has a receptacle for receiving a lighting device at said second end, wherein said optical fiber bundle further directs light from said receptacle to said common output.

12. The blade assembly according to claim 9, further including a lighting device supported by said body blade, wherein said optical fiber bundle further directs light from said lighting device to said common output.

13. The blade assembly according to claim 9, further including a handle adaptor that selectively attaches to said blade body at one of said handle attachment points.

14. The system according to claim 9, wherein said handle attachment points are at different distances from said distal end of said blade body wherein said different distances correspond in length to standard sizes of laryngoscope blades.

15. A method of selectively adjusting the functional length of a laryngoscope blade in a laryngoscope system, comprising:
   providing a blade body having a distal end, an opposite second end and a plurality of handle attachment points between said distal end and said second end;
   providing a handle;
   selectively attaching said handle to one of said handle attachment points on said blade body to set said handle at a selected distance from said distal end of said blade body.

16. The method according to claim 15, further including providing an optical fiber bundle on said blade body that direct light from said handle attachment points to a common output.

17. The method according to claim 16, wherein providing a handle includes providing a handle with an internal lighting element that shines light into one of said handle attachment points when said handle is attached to one of said handle attachment points.

\* \* \* \* \*